US011598761B2

(12) United States Patent
Alves Fortunato et al.

(10) Patent No.: US 11,598,761 B2
(45) Date of Patent: Mar. 7, 2023

(54) DEVICE FOR MEASURING THE OXIDATION STABILITY AND/OR THE THERMAL STABILITY OF A FUEL BY MEANS OF A MICROFLUIDIC CHIP

(71) Applicant: IFP Energies nouvelles, Rueil-Malmaison (FR)

(72) Inventors: Maira Alves Fortunato, Carrieres sur Seine (FR); Laurie Starck, Rueil Malmaison (FR); Aurelie Mouret, Cormeilles en Parisis (FR); Christine Dalmazzone, Viroflay (FR); Nicolas Pannacci, Paris (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 405 days.

(21) Appl. No.: 16/646,795

(22) PCT Filed: Aug. 30, 2018

(86) PCT No.: PCT/EP2018/073335
§ 371 (c)(1),
(2) Date: Mar. 12, 2020

(87) PCT Pub. No.: WO2019/052826
PCT Pub. Date: Mar. 21, 2019

(65) Prior Publication Data
US 2020/0264155 A1 Aug. 20, 2020

(30) Foreign Application Priority Data
Sep. 13, 2017 (FR) ...................................... 1758485

(51) Int. Cl.
*G01N 33/22* (2006.01)
*G01N 33/28* (2006.01)
(Continued)

(52) U.S. Cl.
CPC ............... *G01N 33/28* (2013.01); *G01F 1/00* (2013.01); *G01L 13/00* (2013.01); *G01N 21/31* (2013.01)

(58) Field of Classification Search
CPC .... G01N 33/22; G01N 33/2805; G01N 21/31; G01N 33/28; G01L 13/00; G01F 1/00
(Continued)

(56) References Cited

U.S. PATENT DOCUMENTS 3,670,561 A * 6/1972 Hundere ............ G01N 33/2805
73/61.62
4,595,824 A * 6/1986 Harvey ................... F24H 1/142
374/45
(Continued)

FOREIGN PATENT DOCUMENTS

WO 95/02821 A1 1/1995
WO 2016/050636 A1 4/2016

OTHER PUBLICATIONS

Serio, M. et al, SPIE 1993, 2069, 20-31.*
(Continued)

*Primary Examiner* — Arlen Soderquist
(74) *Attorney, Agent, or Firm* — Fitch, Even, Tabin & Flannery LLP

(57) ABSTRACT

The present invention relates to a device (1) for measuring the oxidation stability and/or the thermal stability of any type of fuel, including diesel fuel, by miniaturization of the test system by use of a microfluidic technique. The physical phenomena to which fuels are subjected are reproduced by the microchannels (12) of the microfluidic chip (7), which comprise a representation of at least one of the fuel injection and the fuel circulation for a drive system, an internal-combustion engine or an aircraft reactor for example.

17 Claims, 1 Drawing Sheet

(51) Int. Cl.
   *G01N 21/31* (2006.01)
   *G01F 1/00* (2022.01)
   *G01L 13/00* (2006.01)

(58) Field of Classification Search
   USPC .......................................................... 436/60
   See application file for complete search history.

(56) References Cited

U.S. PATENT DOCUMENTS

| | | | | |
|---|---|---|---|---|
| 4,832,857 | A * | 5/1989 | Hunt | C10M 159/22 508/393 |
| 4,842,410 | A * | 6/1989 | Darrah | G01N 33/2805 356/505 |
| 5,101,658 | A * | 4/1992 | Wilson, III | G01N 33/2805 73/61.62 |
| 5,287,731 | A * | 2/1994 | Florkowski | G01N 33/2817 422/53 |
| 5,293,218 | A | 3/1994 | Morris et al. | |
| 5,299,449 | A * | 4/1994 | Hardy | G01N 33/2805 73/61.62 |
| 5,337,599 | A * | 8/1994 | Hundere | G01N 33/2805 73/61.62 |
| 6,370,946 | B1 * | 4/2002 | Lacey | G01N 5/02 73/61.62 |
| 2005/0183496 | A1 * | 8/2005 | Baek | G01N 11/08 73/54.09 |
| 2006/0263893 | A1 * | 11/2006 | Moses | G01N 33/2805 436/143 |
| 2008/0134765 | A1 * | 6/2008 | Baek | G01N 11/08 73/54.09 |
| 2009/0233817 | A1 * | 9/2009 | Kriegel | C10L 10/14 73/61.76 |
| 2010/0115952 | A1 * | 5/2010 | Sako | F02C 7/22 73/1.01 |
| 2013/0125627 | A1 * | 5/2013 | Yuan | G01N 11/08 73/54.01 |
| 2017/0246632 | A1 | 8/2017 | Slepian et al. | |
| 2019/0162640 | A1 * | 5/2019 | Lépinay | B01D 53/26 |

OTHER PUBLICATIONS

Altin, O. et al, Industrial & Engineering Chemistry Research 2001, 40, 596-603.*
Eser, S. et al, Industrial & Engineering Chemistry Research 2006, 45, 8946-8955.*
Venkataraman, R. et al, Industrial & Engineering Chemistry Research 2008, 47, 9337-9350.*
Yang, K. et al., Thesis 2012, 72 pages.*
Tu, Q. et al, Chinese Journal of Chemistry 2013, 31, 304-316.*
Borecki, M. et al, International Journal on Advances in Systems and Measurements 2014, 7, 57-67.*
Burggraf, F. et al, SAE Transactions 1966, 74, paper 650114, 504-512.*
Vranos, A. et al, NASA. Lewis Res. Center Aircraft Res. and Technol. for Future Fuels 1980, 169-179.*
Szetela, E. J, et al, Turbo Expo: Power for Land, Sea, and Air 1985, 85-IGT-130, 7 pages.*
Nickolaus, D. et al, Journal of Propulsion 1987, 3, 502-507.*
Chin, J. S. et al, Journal of Propulsion and Power 1992, 8, 1152-1156.*
Linne, D. L. et al, "Evaluation of Heat Transfer and Thermal Stability of Supercritical JP-7 Fuel" National Aeronautics and Space Administration, Lewis Research Center 1997, 17 pages.*
Spadaccini, L. J. et al, Journal of Engineering for Gas Turbines and Power 2001, 123, 741-746.*
Liu, Z. et al, Applied Thermal Engineering 2013, 51, 1047-1054.*
Morris, R. W. et al, Report AFRL-RQ-WP-TR-2015-0014 2014, 163 pages.*
Yuen, F. T. C. et al, Energy & Fuels 2017, 31, 3585-3591.*
International Search Report for PCT/EP2018/073335, dated Dec. 4, 2018; English translation submitted herewith (7 pgs.).
Cunha H N et al: "The interaction of ozone with bio-fuel, revealed by electrical conduction and infared spectroscopy", Fuel Processing Technology, Elsevier BV, NL, vol. 92, No. 11, Jun. 6, 2011 (Jun. 6, 2011).
Michal Borecki et al: "Capillary Sensor with UV-VIS Reading of Effects of Diesel and Biodiesel Fuel Degradation in Storage", Sensors & Transducers, Oct. 31, 2016 (Oct. 31, 2016), pp. 1-9.

* cited by examiner

//]: #

DEVICE FOR MEASURING THE OXIDATION STABILITY AND/OR THE THERMAL STABILITY OF A FUEL BY MEANS OF A MICROFLUIDIC CHIP

CROSS-REFERENCE TO RELATED APPLICATIONS

Reference is made to International Application No. PCT/EP2018/073335, filed Aug. 30, 2018, which claims priority to French Patent application Ser. No. 17/58,485, filed Sep. 13, 2017, the contents of which are incorporated herein by reference in their entirety.

BACKGROUND OF THE INVENTION

Field of the Invention

The present invention relates to the field of fuel analysis and characterization, notably for a fuel of diesel, biodiesel, gasoline or jet fuel (aviation fuel also referred to as kerosene through misuse of language) type and specifically to a characterization device allowing at least one of the oxidation stability and the thermal stability of a fuel to be measured.

Description of the Prior Art

The stability of fuels has generated considerable interest among actors in the field of aeronautics and land vehicles, as well as refining because, on the one hand, of the diversification of fuels (fuels derived from crude oil, alternative fuels and biofuels) and processes and, on the other hand, of technological developments.

For example, in the automotive field, the emission standards imposed on vehicles motivate manufacturers to develop increasingly efficient engines in order to reduce emissions at source, that is from combustion, which results in a current combustion engine technology with increasingly stringent operating conditions for diesel injection systems, with an increase in thermal stresses (T>150° C.), a pressure increase (P>2500 bar), combined with a decrease in the diameter of the injector holes.

In the aeronautical field, the temperature and pressure rise cycles imposed on the fuel, combined with increasingly severe conditions, are critical for maintaining a stable product.

In the logistics field, it appears that the logistics chain becomes more and more complex with many different products associated with various new additives.

These different points require a very detailed characterization of the thermal stability of a fuel to avoid problems related to the degradation of fuels in the automotive, aeronautical and logistics refining fields (e.g. deposits). Currently, there is an increasing demand from the automotive industry (car manufacturers, equipment manufacturers, petroleum industry, etc.), notably in Europe, for a thermal stability characterization more representative of the new stresses undergone by fuels.

Today, there is no certified technique for studying the loss of thermal stability and the formation of diesel fuel deposits under dynamic conditions. This is related to the complexity of the various engine configurations and to the difficulty of finding a representative test. Diesel fuel characterizations are rather focused on oxidation stability, with for example the PetroOxy (according to the ASTM 7545 standard) and Rancimat (according to the EN15,751 standard) methods. In the case of the aeronautical industry, the thermal stability of jet fuels is controlled and measured through the JFTOT™ test (Jet Fuel Thermal Oxidation Tester). An example of this method is described in U.S. Pat. No. 5,293,218 and in the ASTM D3241-14be1 standard method. The JFTOT™ test circulates a jet fuel around a heated tube. However, a JFTOT™ type test dedicated to diesel fuels does not currently exist in the standard and the fuel specification. Furthermore, this equipment involves the drawback of being bulky and difficult to interpret. It may also be added that the results obtained with this method are not representative of what is found in the real system, notably regarding the choice of materials. Besides, the JFTOT™ type test requires a significant amount of fuel and a secure environment.

In order to reduce the size of the device, some fuel testing devices use microfluidic chips. An example of such a fuel oxidation testing device is described in patent application BR PI 1,002,057-8 A2. The specific test described in this document concerns an accelerated oxidation through ozone injection. However, the device described in this patent application is complex because it requires injecting ozone into the fuel. Furthermore, the microfluidic cell, which has a unique pattern, does reproduce the physical phenomena to which the fuels are subjected in reality.

SUMMARY OF THE INVENTION

To overcome these drawbacks, the present invention relates to a device for measuring at least one of the oxidation stability and the thermal stability of any type of fuel, including diesel fuel, by miniaturization of the test system by use of the microfluidic technique. The physical phenomena to which fuels are subjected are reproduced by the microchannels of the microfluidic chip, which comprise representing at least one of the fuel injection and the fuel circulation for a drive system, an internal-combustion engine or an aircraft reactor for example.

The invention relates to a device for measuring at least one of the oxidation stability and the thermal stability of a fuel. The measuring system comprises a fuel supply, a microfluidic chip, a fuel circulator for circulating the fuel within the microfluidic chip from the fuel supply, and a measuring system for measuring at least one of the oxidation stability and the thermal stability of the fuel. The measuring system is connected to the microfluidic chip. The microfluidic chip comprises a microchannel circuit for circulation of the fuel, the microchannels comprises representation of the at least one of the injection and the circulation of the fuel for a drive system such as an internal-combustion engine or a reactor.

According to an embodiment of the invention, the representation of the injection or the circulation of a fuel includes at least using shearing the fuel.

Advantageously, the fuel shearing comprises at least one restriction in the diameter of a microchannel for circulating the fuel.

According to an implementation, the representation further comprises at least one of a diversion microchannel and a predetermined shape of circulation microchannel for the fuel.

Advantageously, the dimensions of the microfluidic chip range between 10×20 mm and 50×100 mm.

According to an aspect of the invention, the measuring device comprises measuring the flow of the fuel to determine a variation in a physical property of the fuel.

Advantageously, the measuring device of the flow of the fuel comprises a flowmeter, at least one pressure sensor, a pressure differential sensor and control for controlling a deposit formed in the microfluidic chip.

Furthermore, the measuring device comprises at least one spectrometer.

Advantageously, the microfluidic chip is made of glass or metal.

Preferably, the fuel is a jet fuel, diesel, biodiesel, biofuel, alternative fuel, a refined cut or type of gasoline.

According to an aspect of the invention, the measuring device comprises a heater for heating the microfluidic chip.

According to a feature, the circulator for circulating the fuel includes a syringe driver.

Furthermore, the invention relates to a system for testing a fuel, comprising a measuring device according to one of the above features, connected to a reserve of the fuel.

The invention further relates to a fouling sensor arranged within an internal-combustion engine or a reactor. The fouling sensor comprises a measuring device according to one of the above features.

BRIEF DESCRIPTION OF THE DRAWINGS

Other features and advantages of the device according to the invention will be clear from reading the description hereafter of embodiments given by way of non-limitative example, with reference to the accompanying figures wherein.

DETAILED DESCRIPTION OF THE INVENTION

Figure 1:
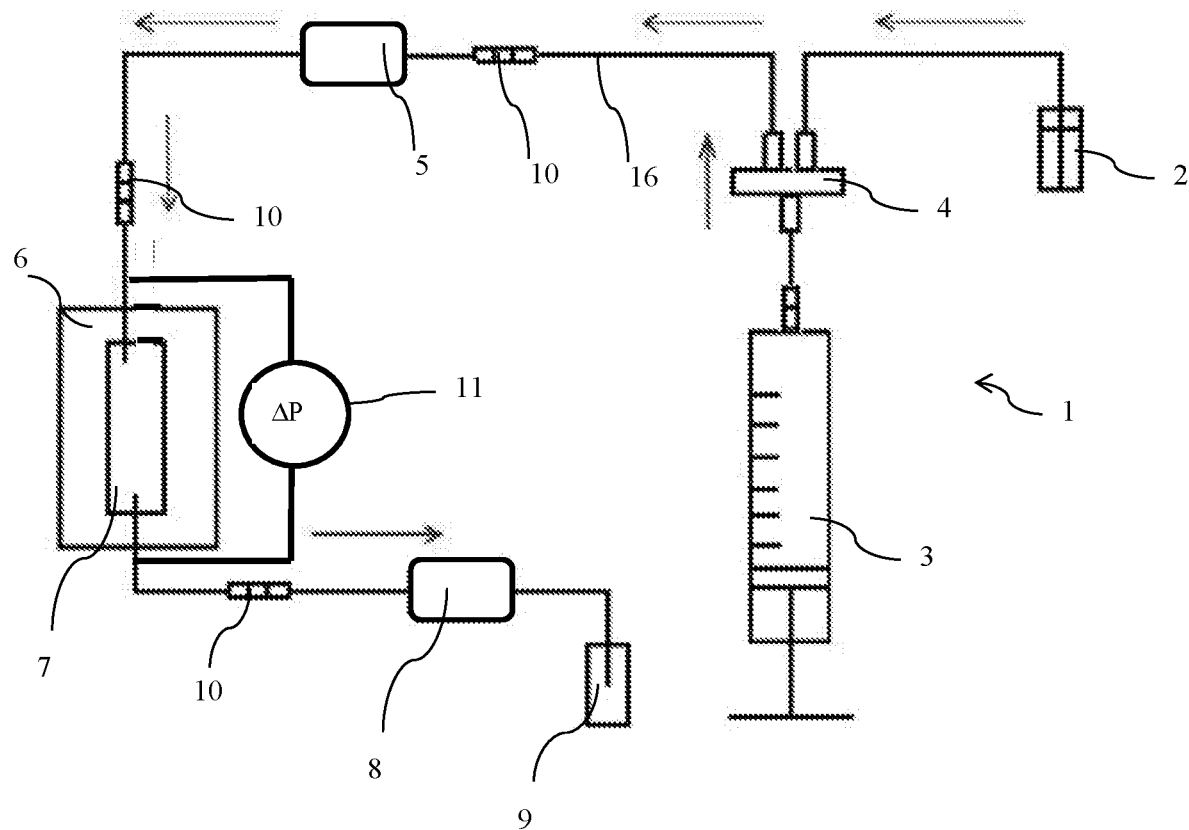
FIG. 1 illustrates a measuring device according to an embodiment of the invention.

The present invention relates to a device for measuring at least one of the oxidation stability and the thermal stability of a fuel. The device according to the invention notably allows measurement of deposits, such as fouling, originating from a fuel under specific conditions, which correspond to the conditions of use of the fuel. Thus, the device according to the invention can be used to analyze problems of clogging and formation of deposits such as varnish, gum, lacquer and coke within a drive system.

Oxidation stability or auto-oxidation is understood to be the tendency of a fuel to degrade from the oxidation of its compounds by contact with oxygen.

Thermal stability or thermo-oxidation is understood to be the characteristic of a fuel to degrade or to decompose from exposure to high temperatures in a medium with or without oxygen. It can be noted that temperature has a direct effect on the decomposition reaction kinetics of a fuel.

A drive system is understood to be a system capable of converting the chemical energy of a fuel into mechanical energy. In particular, it can be an internal-combustion engine or an aircraft reactor (aircraft turbine engine).

The tested fuel can be of any type, in particular diesel, biodiesel, gasoline, biofuel, alternative fuel or jet fuel.

The system according to the invention comprises at least:
- a supply for the fuel to be tested, it may notably be a fuel reserve or a connection to a fuel supply system;
- a microfluidic chip, which comprises microchannels through which the fuel flows, and within which the fuel is degraded and/or forms deposits;
- a circulation system for circulating the fuel within the microfluidic chip from the supply; and
- a measuring system connected to the microfluidic chip, capable of measuring at least one characteristic of the fluid circulating in at least one of the microfluidic chip and a characteristic related to the deposit (fouling) in the microfluidic chip.

A microfluidic chip is a network of microchannels engraved or moulded in a material (for example glass (ranging from quartz to molten silica, along with soda-lime and borosilicate glass), silicon, metal or polymer such as PDMS, for PolyDiMethylSiloxane, or photosensitive resins such as SU-8, or thermoplastic polymers such as PMMA or PEEK). Conventionally, the microchannels that make up the microfluidic chip are connected to one another to fulfill a desired function (mixing, pumping, sorting, biochemical environment control, measurement, chemical analyses). This network of microchannels enclosed in the microfluidic chip is connected to the outside by at least one inlet and at least one outlet of the microchannel through the chip, like interfaces between the macroscopic and the microscopic world. It is through these holes that the fuel is injected into and discharged from the microfluidic chip (through tubes, syringe adapters or even simple holes in the chip) with external active systems (pressure controller, syringe driver or peristaltic pump) or passive system (hydrostatic pressures for example). A microfluidic chip can operate under pressure.

According to the invention, the microchannels of the microfluidic chip comprise representation of at least one of the injection and circulation of the fuel in a drive system (an internal-combustion engine or a reactor for example). Fuel circulation is understood to be the entire system allowing the fuel tank to be connected to the drive system in a vehicle (automotive or aircraft). Thus, it is possible to reproduce ("simulate") physical phenomena and to perform measurements representative of the real conditions of use of the fuel within a drive system. It is thus possible to precisely quantify the oxidation stability and the thermal stability of a fuel.

In order to best reproduce physical phenomena, the microchannels of the microfluidic chip can comprise the following representations, alone or in combination:
- at least one restriction in the diameter of a fuel circulation microchannel, which can notably allow the injection of fuel or the presence of a valve to be represented;
- at least one fuel diversion microchannel (in other words, separation of the fuel in at least two parallel microchannels) which can notably allow representation of a portion of a fuel supply circuit of a drive system; and
- at least one predetermined shape of a microchannel such as for example a curvature of the microchannel which can notably allow representation of a curved portion of a fuel supply circuit of a drive system.

Preferably, the representation can comprise at least one representation of a restriction generating fuel shearing. Shearing is typically encountered upon passage of the fuel through an injector for an application in the automotive field (diesel fuel and gasoline) as well as the aeronautical field (kerosene). Thus, the microfluidic chip allows performing measurements representative of the real conditions of use of the fuel in an injection system. It is thus possible to precisely quantify the impact of the evolution of the oxidation stability and the thermal stability of a fuel in a microfluidic system as representative as possible of a real fuel circuit.

Such a representation of generation of shearing can preferably be a restriction in the diameter of a microchannel (whatever the type of restriction: shoulder, frustoconical part, etc.).

The microfluidic chip advantageously has reduced dimensions in relation to systems of the prior art.

With a view to miniaturization of the measuring device, the dimensions of the microfluidic chip range between 10×20 mm and 50×100 mm. Furthermore, the microchannels can have diameters ranging between 10 μm and 1000 μm. The microchannels can have lengths ranging between a few centimeters and a few meters.

Preferably, the microchannels are substantially cylindrical and of circular section to limit pressure drops. However, the microchannels can have any shape suited to fluid circulation such as for example a cylindrical and an elliptic section, parallelepipedic, etc.

According to an embodiment of the invention, the measuring device connected to the microfluidic chip can comprise the following elements, alone or in combination:
at least one flowmeter is downstream or upstream from the microfluidic chip (according to the direction of flow of the fuel). According to an example embodiment, the measuring device can comprise two flowmeters, one upstream from the microfluidic chip and one downstream from the microfluidic chip which allows measuring the flow rate evolution induced by the fuel degradation and the formation of deposits within the microfluidic chip, notably when working with a controlled pressure pump (of Fluigent flow control system type);
at least one pressure sensor downstream, upstream from, or within, the microfluidic chip (according to the direction of flow of the fuel). According to an example embodiment, the measuring device can comprise two pressure sensors with one upstream from the microfluidic chip and one downstream from the microfluidic chip, or a differential pressure sensor which allows measuring the evolution of the pressure drop induced by the fuel degradation or the formation of deposits within the microfluidic chip, when working with a flow control pump such as a syringe driver or a piston;
a spectrometer for measuring the ageing of the fuel within the microfluidic chip. For example infrared, UV, fluorescence, etc., a spectrometer measures only the chemical properties of the fuel;
at least one of online viscosity and/or density measuring device,
a control for controlling the deposit formed in the microfluidic chip with deposit control being:
an optical measuring device for real-time (for example if the microfluidic chip is made of glass) or ex-situ measurement, intended to measure at least one of the thickness, the color and the volume of the deposit, for example by use of one of interferometry or ellipsometry, described in the ASTM D3241 standard; and
a mass measurement device for measuring the mass of the deposit.

At least one of flow rate pressure measurements for determining whether an oxidation exists or not, through analysis of at least one of the flow rate and the pressure variations.

According to an aspect of the invention, the flow rate and pressure measurements can be performed in real time.

Advantageously, the measurements perform fuel flow measurements. It is thus possible to measure the impact of a variation in the physical properties of the fuel on the flow measurements. These flow measurements can be performed using a flowmeter, a pressure or pressure differential sensor, a viscosity measuring device, and deposit controls.

According to an implementation of the invention, the microfluidic chip can be made of glass because of its compatibility with fuels and the conditions of use thereof. Furthermore, this material facilitates measurements, in particular optical measurements.

Alternatively, the microfluidic chip can be made of metal because this material is compatible with fuels and the conditions of use thereof. Moreover when the metal corresponds to the materials used in the drive systems, a microfluidic chip made of metal provides good measurement representativeness.

According to an aspect of the invention, the measuring device comprises a heater for heating the microfluidic chip, for example at least one resistor. The heater allows heating the fuel circulating in the microfluidic chip in order to make the conditions of flow of the fuel in the microfluidic chip more severe. Thus, measurement of the oxidation stability and more particularly measurement of the thermal stability are accurately determined.

For example, the heater allows the microfluidic chip to be heated to temperatures ranging between 25° C. and 300° C., preferably between 50° C. and 200° C.

According to an implementation of the invention, the measuring device can include microfluidic chips. It is thus possible to perform measurements for various fluid conditions. In particular, each microfluidic chip can have a heater which can be set at different temperatures.

According to an example embodiment, the microfluidic chips can be in parallel.

Alternatively, the microfluidic chips can be in series. This configuration allows the size of the measuring device to be limited.

According to an embodiment of the invention, the circulator for circulating the fluid in the microfluidic chip can regulate the flow rate of the fuel flowing through the microfluidic chip.

In order to regulate the flow rate of the fluid circulating in the microfluidic chip, the fuel circulation can be provided by a syringe driver (with a volume ranging between 10 μL and 50 μL), which is suited to the small volumes and flow rates implemented by the device according to the invention.

In a variant, the fuel circulation system can be a pump, a peristaltic pump for example, or a controlled pressure pump (of Fluigent flow control system type).

Advantageously, the measuring device can further comprise at least one of the following equipments:
a tank containing a sample of the fuel to be tested;
a filter for preventing transport of the deposit, which can be used to measure the deposit collected by the filter;
a measurement automation system for controlling the fuel circulation and the measuring;
a flushing circuit for cleaning the device between two measurements; and
an analysis module for grouping the measurements, etc.

Advantageously, it is possible to use a diesel type fuel, notably because of the materials used for the microfluidic chip, the measurement temperatures and the use of optional filters.

FIG. 1 schematically illustrates, by way of non-limitative example, a measuring device 1 according to an embodiment of the invention. Measuring device 1 comprises a fuel inlet 2 (a fuel reserve for example) supplying a syringe pump 3 using a three-way valve 4. Then, by actuating syringe pump 3, the fuel is fed to microfluidic chip 7 through lines 16. Various line sections 16 are connected together by connectors 10. Connectors 10 enable adaptation to different diameters of the lines. Microfluidic chip 7 is mounted on a support 6. The microfluidic chip can have a fuel inlet diameter of 500 μm and a fuel outlet diameter of 100 μm. A diameter restriction (not shown) for example is provided between the inlet and the outlet of the microfluidic chip. Support 6 can comprise a heater (not shown) for heating the fuel flowing through microfluidic chip 7. For the fluid measurement, two flowmeters 5 and 8 are provided, as well as a differential pressure sensor 11 on either side of the chip. Upstream from microfluidic chip 7 the first flowmeter 5 measures the fuel flow rate. Furthermore, the second flowmeter 8 is provided downstream from microfluidic chip 7. It is thus possible to measure the flow rate difference between the inlet and the outlet of microfluidic chip 7 for checking for leaks and monitoring the pressure drop evolution via differential pressure sensor 11. Measuring device 1 further comprises a fuel outlet 9 which collects the tested fuel. According to an embodiment of the invention, it is possible to operate in a closed loop by providing recirculation of the fluid between outlet 9 and inlet 2, using a peristaltic pump for example.

Figure 2:
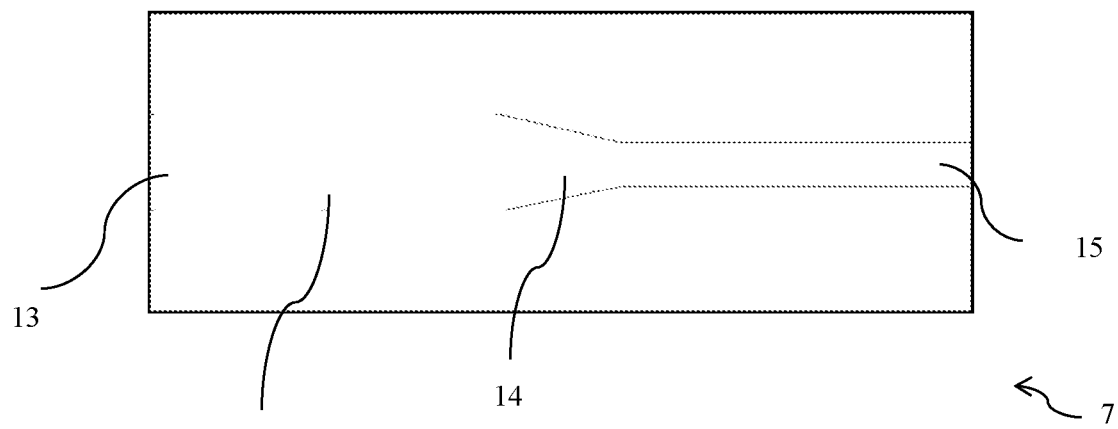
FIG. 2 illustrates an example of a microfluidic chip according to an embodiment of the invention.

FIG. 2 schematically illustrates, by way of non-limitative example, a microfluidic chip according to an embodiment of the invention. The microfluidic chip 7 comprises a single rectilinear microchannel 12. Microchannel 12 comprises a fuel inlet 13, a diameter restriction 14 and a fuel outlet 15 which has an outlet 15 having a diameter being smaller than the diameter of inlet 13. The microfluidic chip can be used to represent the injection of fuel (diesel for example) into an internal-combustion engine or a reactor.

The present invention also relates to a fuel testing system comprising a measuring device according to one of the variants described above or a combination of variants described above. The fuel testing system can be connected to a fuel reserve.

Thus, the measuring device can be used for testing for example the selection of a fuel according to the conditions of use.

Furthermore, the present invention relates to a fouling sensor comprising a measuring device according to one of the variants described above or a combination of variants described above. The fouling sensor can be arranged within a drive system such as an internal-combustion engine or a reactor or an aircraft turbine engine. Moreover, the fouling sensor can be arranged on-board a vehicle which is land or aeronautical for example.

Thus, the fouling sensor provides detection of fouling of the drive system after detecting a deposit in the measuring device. It can be installed within the drive system due to the dimensions of the microfluidic chip.

The invention claimed is:

1. A system for measuring at least one of oxidation stability and thermal stability of fuel, the system comprising a fuel supply, a microfluidic chip, a circulation system for circulating the fuel within the microfluidic chip from the fuel supply, and a measuring system for measuring at least one of the oxidation stability and thermal stability of the fuel, the measuring system being connected to the microfluidic chip, the microfluidic chip comprising a microchannel circuit for circulation of the fuel, the microchannel circuit comprising a representation of at least one of injection and circulation of the fuel for a drive system of an engine or a reactor, and includes a system for measuring flow rate variation caused by fuel degradation and formation of deposits in the microfluidic chip of flow of the fuel caused by variation of a physical property of the fuel, including two flowmeters which are respectively upstream and downstream from the microfluidic chip.

2. A system as claimed in claim 1, wherein the representation of at least one of the injection and the circulation of the fuel includes at least one means for shearing the fuel.

3. A system as claimed in claim 2, wherein the means for shearing comprises at least one restriction in diameter of a microchannel circuit for circulating the fuel.

4. A system as claimed in claim 3, wherein dimensions of the microfluidic chip range between 10×20 mm and 50×100 mm.

5. A system as claimed in claim 2, wherein the representation further comprises at least one diversion microchannel for at least one of the fuel and shape of a circulation microchannel for the fuel.

6. A system as claimed in claim 2, wherein dimensions of the microfluidic chip range between 10×20 mm and 50×100 mm.

7. A system as claimed in claim 1, wherein the representation further comprises at least one diversion microchannel for at least one of the fuel and shape of a circulation microchannel for the fuel.

8. A system as claimed in claim 7, wherein dimensions of the microfluidic chip range between 10×20 mm and 50×100 mm.

9. A system as claimed in claim 1, wherein dimensions of the microfluidic chip range between 10×20 mm and 50×100 mm.

10. A system as claimed in claim 1, wherein the measuring system comprises at least one spectrometer.

11. A system as claimed in claim 1, wherein the microfluidic chip comprises glass or metal.

12. A system as claimed in claim 1, wherein the fuel comprises one of jet fuel, diesel, biodiesel, biofuel, alternative fuel, a refined cut and gasoline.

13. A system as claimed in claim 1, comprising a heater for heating the microfluidic chip.

14. A system as claimed in claim 1, wherein the circulation system comprises a syringe driver.

15. A system for testing a fuel, comprising a measuring device as claimed in claim 1, connected to a fuel reserve.

16. A system as claimed in claim 1, wherein the system includes pressure sensors respectively upstream and downstream from the microfluidic chip or a differential pressure sensor in the microfluidic chip.

17. A fouling sensor within an internal-combustion engine or a reactor, comprising a system for measuring as claimed in claim 1.

* * * * *